United States Patent [19]

Moore

[11] Plant 4,230

[45] Mar. 28, 1978

[54] ROSE PLANT

[76] Inventor: Ralph S. Moore, 2519 E. Noble Ave., Visalia, Calif. 93277

[21] Appl. No.: 805,610

[22] Filed: Jun. 10, 1977

[51] Int. Cl.[2] ..... A01H 5/00
[52] U.S. Cl. ..... Plt./3
[58] Field of Search ..... Plt./3

*Primary Examiner*—Robert E. Bagwill

[57] ABSTRACT

The subject of the present invention is a new and distinct variety of miniature rose plant characterized by slender deep yellow buds and flowers of about 20 petals which resist fading even in hot weather and further identified by the rounded, much branched plant with glossy foliage.

1 Drawing Figure

1

The present invention relates to a new and distinct variety of hardy, dwarf, bush type rose plant of the miniature class; the variety being primarily characterized — as to novelty — by deep yellow buds and flowers which in general color effect are similar to Summer Sunshine, a hybrid tea variety (Patent No. 2078).

The variety is further characterized by:

An abundance of bloom, with flowers borne singly or several to the stem in loose clusters.

Sweet rose fragrance.

A plant which is vigorous, of rounded somewhat spreading shape with glossy, small foliage with pointed leaflets; the buds and flowers being similar in form and size to Bit O'Sunshine (miniature — U.S. Plant Pat. No. 1,631, expired).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Golden Glow (U.S. Plant Pat. No. 263, expired), Climber, as the seed parent and Peachy White (miniature — not patented), as the pollen parent.

Subsequent to origination of the variety I successfully asexually reproduced it, in my nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety name: Calgold.

Flowers borne: Singly and several together (3 to 5) on slender wirey stems.

Quantity of bloom: Abundant both outside and in greenhouse.

2

Bud: Peduncle — medium length; slender but sturdy; erect; medium green, sometimes tinted bronze (outdoors); hairs — usually none. Before calyx breaks; size — small. Form long: pointed with few foliaceous apendages and few or no hairs on surface of bud; with foliaceous parts extending beyond the tip of the bud equal to one-half or less of its length. Color — medium green, occasionally tinted with bronze (outdoors). As Calyx breaks, color — deep yellow — near Indian Yellow 6/1 (sometimes greenish at base); occasional outer petals may be tinted with splash of red (similar to Bit O'Sunshine). Opening: opens well in all weather.

Bloom: Size when fully open — small, averaging about 40 mm. Petalage — double — averaging about 20 petals, arranged regularly plus sometimes several small petaloids. Form — cupped at first, becoming more open in the center, with petals rolled loosely outward, and later at maturity open with petals folded at edge to give a pointed effect and rolled loosely outward and downward. Open flowers show stamens.

Petals: Fairly thick; satiny on inside and on outside surface. Shape — outside petals, broad lanceolate (nearly oval) with acute tip; intermediate — broad lanceolate with acute tip; inside — lanceolate with acute tip.

Color: Newly opened flower from a plant grown in plastic greenhouse (April 1977), Visalia, Calif.:

*Outside petal.*—Outside surface — near Lemon Yellow 4/1 becoming slightly greenish toward base. Inside surface — near Lemon Yellow 4/1.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — clear bright yellow. Three days open — color similar to newly opened flowers but lighter color. Behavior — open well in all weather. Yellow color lasts better then most other yellow miniatures. Spent petals drop off. Flower longevity (October 1976) — plant in pot 4–6 days or longer. Cut flowers at living room temperature 3–5 days.

Reproductive organs:

*Stamens.*—Abundant, arranged regularly about pistils.

*Filaments.*—Varying length, fairly long, yellow.
*Anthers.*—Well formed; yellow.
*Pollen.*—Moderate amount.
*Pistils.*—Average number.
*Styles.*—Fairly even; medium length; bunched; color — reddish.
*Ovaries.*—All enclosed in calyx.
*Hips.*—Few.
*Sepals.*—Permanent; spear shaped; recurved.
*Seed.*—Few or none.

Foliage:

*Leaves.*—Compound of five (sometimes three or seven) leaflets; quite small; leathery; semi-glossy.
*Leaflets.*—Shape: broad, nearly oval; apex acute; base rounded or rounded acute. Margin serrate.
*Color.*—Medium green; new growth — normal (medium) green.
*Rachis.*—Medium strength; upper side may have a few tiny short prickles, grooved; underside sparsely thorny with few or no tiny prickles.
*Stipules.*—Medium long; narrow to medium width; medium length narrow points which turn out usually at about 45°.

Growth:

*Habit.*—Dwarf; bushy; rounded; much branched.
*Growth.*—Free vigorous; internodes short.
*Canes.*—Medium; slender; sturdy.

*Main stems.*—Color: light to medium green.
*Thorns.*—Average; slender; hooked slightly downward; color; brown. Prickles — none. Hairs — none.
*Branches.*—Color: light to medium green. Thorns: few; short length; slender; nearly straight. Medium to short oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers which are clear deep yellow in color with an occasional guard (outer) petal splashed with red, the bud and flower resembling Bit O'Sunshine (miniature — U.S. Plant Pat. No. 1,631) in size and shape; and further characterized by a plant which is vigorous and compact, easy to propagate from cuttings or by budding, with an abundance of small to medium size semi-glossy foliage and an abundance of flowers borne singly or several to the stem in loose clusters.

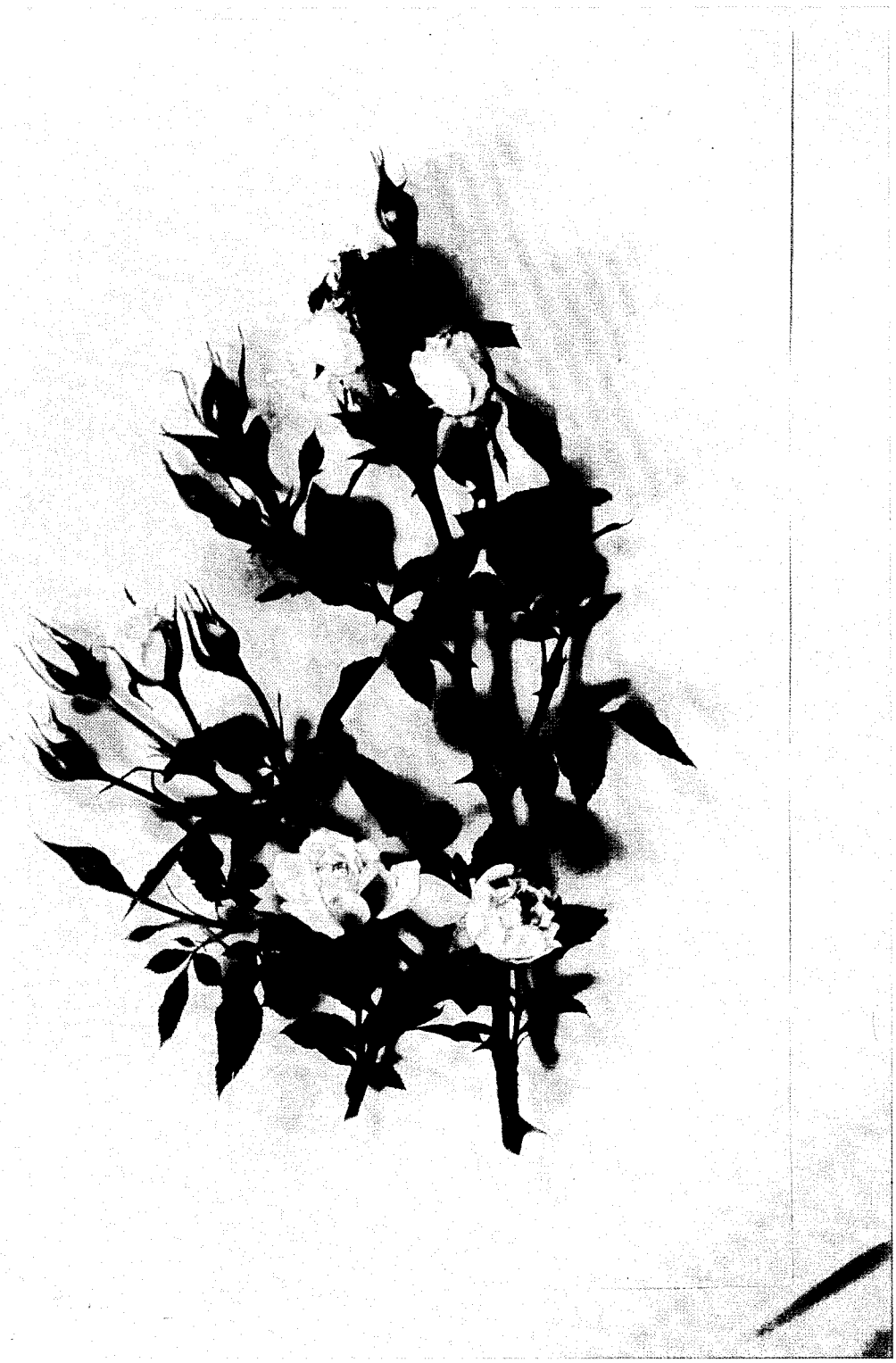

* * * * *